United States Patent
Moe et al.

(10) Patent No.: US 6,613,086 B1
(45) Date of Patent: *Sep. 2, 2003

(54) ALTERING HEART VALVE LEAFLET ATTACHMENT GEOMETRY TO INFLUENCE THE LOCATION AND MAGNITUDE OF MAXIMUM LOADED STRESS ON THE LEAFLET

(75) Inventors: Riyad E. Moe, Austin, TX (US); John Kenneth Ryder, Round Rock, TX (US)

(73) Assignee: CarboMedics Inc., Austin, TX (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/523,804

(22) Filed: Mar. 13, 2000

Related U.S. Application Data (63) Continuation-in-part of application No. 09/103,482, filed on Jun. 24, 1998, now abandoned.

(51) Int. Cl.[7] .................................................. A61F 2/24
(52) U.S. Cl. ........................................ 623/2.12; 623/2.1
(58) Field of Search ................................. 623/2.1, 2.12, 623/2.14, 2.17, 2.18, 2.19, 2.28, 2.29, 2.33; 606/194

(56) References Cited

U.S. PATENT DOCUMENTS

| | | | |
|---|---|---|---|
| 3,714,671 A | 2/1973 | Edwards et al. | ..................... 3/1 |
| 4,470,157 A | 9/1984 | Love | ............................... 3/1.5 |

(List continued on next page.)

FOREIGN PATENT DOCUMENTS

| WO | WO 97/41808 | 11/1997 |
|---|---|---|
| WO | WO 97/49356 | 12/1997 |

OTHER PUBLICATIONS

Christie, G. W., et al., "On Stress Reduction in Bioprosthetic Heart Valve Leaflets by the US of a Flexible Stent", Journal of Cardiac Surgery, vol. 6, No. 4, pp. 476–481, 1991.
Christie, G. W., et al., "Stress–Related Failure Modes of Bovine Pericardial Heart Valves", Bioprostheses: Design & Material, pp. 765–779.
Clift, S. E., et al., "Finite Element Stress Analysis of a New Design of Synthetic Leaflet Heart Valve", Journal of Engineering in Medicine, vol. 210, pp. 267–272, 1996.
Chandran, K.B., et al., "Stress Distribution on the Cusps of a Polyurethane Trileaflet Heart Valve Prosthesis in the Closed Position ",J. Biomechanics, vol. 24, No. 6, pp. 385–395, 1991.
Christie, G.W., "The Bovine Pericardial Bioprosthetic Heart Valve: Methods for Tensile Stress Reduction in the Leaflets During the Loaded Phase",Advances in Bioengineering, BED–vol. 20, pp. 647–650, 1991.

*Primary Examiner*—Corrine McDermott
*Assistant Examiner*—Alvin Stewart
(74) *Attorney, Agent, or Firm*—Timothy L. Scott; Williams, Morgan & Amerson, P.C.

(57) ABSTRACT

A tri-leaflet prosthetic cardiac valve with leaflets having an analytic shape in a selected position. The leaflets are connected to a valve body at attachment curves. The shape of the leaflet is selected from a set of geometries that can be represented mathematically. The attachment curve is selected to improve the durability of the tri-leaflet valve by moving the point of maximum loaded stress along the attachment curve away from the commissures. An inner wall of the valve body is given a non-circular shape near the attachment curve, the shape of the inner wall corresponding to the attachment curve. Also, a method of making a valve by selecting an analytic leaflet shape, selecting an attachment curve to improve durability of the valve by moving the point of maximum loaded stress along the attachment curve away from the commissures, and forming a valve body to support one or more leaflets, the valve body having a non-circular inner wall conforming to the attachment curve.

19 Claims, 10 Drawing Sheets

U.S. PATENT DOCUMENTS

| | | | |
|---|---|---|---|
| 4,626,255 A | 12/1986 | Reichart et al. | 623/2 |
| 4,759,758 A | 7/1988 | Gabbay | 623/2 |
| 4,778,461 A | 10/1988 | Pietsch et al. | 623/2 |
| 5,500,016 A | 3/1996 | Fisher | 623/2 |
| 5,562,729 A | 10/1996 | Purdy et al. | 623/2 |
| 5,607,442 A * | 3/1997 | Fischell et al. | 606/191 |
| 5,716,417 A * | 2/1998 | Girard et al. | 623/2.17 |
| 5,776,161 A * | 7/1998 | Globerman | 606/194 |
| 5,861,028 A | 1/1999 | Angell | 623/2 |
| 5,895,420 A | 4/1999 | Mirsch, II et al. | 623/2 |
| 5,928,281 A | 7/1999 | Huynh et al. | 623/2 |
| 5,935,163 A | 8/1999 | Gabbay | 623/2 |
| 6,051,022 A * | 4/2000 | Cai et al. | 623/2.15 |
| 6,179,869 B1 * | 1/2001 | Otto | 623/2.33 |
| 6,328,763 B1 * | 12/2001 | Love et al. | 623/2.15 |

* cited by examiner

ALTERING HEART VALVE LEAFLET ATTACHMENT GEOMETRY TO INFLUENCE THE LOCATION AND MAGNITUDE OF MAXIMUM LOADED STRESS ON THE LEAFLET

This application is a continuation in part of U.S. patent application Ser. No. 09/103,482, filed Jun. 24, 1998 now abandoned, which is incorporated herein by reference in its entirety.

TECHNICAL FIELD

The present invention pertains to valves and in particular to tri-leaflet heart valve prostheses.

BACKGROUND ART

Ever since 1950, when blood oxygenators made open heart surgery feasible, it has been possible to treat some forms of heart disease by replacing one of the patient's heart valves with a prosthetic valve. Early heart valve prostheses included ball-and-cage valves in which a ball or disc was housed in a cage. One side of the cage provided an orifice through which blood flowed either into or out of the heart, depending on the valve being replaced. When blood flowed in a forward direction, the energy of the blood flow forced the ball or disc to the back of the cage allowing blood to flow through the valve. When blood attempted to flow in a reverse direction, or "regurgitate", the energy of the blood flow forced the ball or disc into the orifice in the valve and blocked the flow of blood.

Bi-leaflet heart valves were developed to overcome some of the deficiencies of early cage-based designs. A bi-leaflet valve comprises an annular valve body in which two opposed leaflet occluders are pivotally mounted. The occluders are typically substantially rigid, although some designs incorporate flexible leaflets, moving between a closed position in which the two leaflets are mated to prevent blood flow in the reverse direction, and an open position in which the occluders are pivoted away from each other to permit blood flow in the forward direction. The energy of blood flow caused the occluders to move between their open and closed positions.

Tri-leaflet heart valves are another type of valve developed to overcome deficiencies of prior valve designs. A tri-leaflet valve comprises an annular valve body in which three flexible leaflets are mounted to a portion of the valve body, called a "stent", located at the circumference of the annulus. Although some tri-leaflet valves use rigid leaflets, flexible leaflets are typical. When blood flows in the forward direction, the energy of the blood flow deflects the leaflets away from the center of the annulus and allows blood to flow through the valve body in the forward direction. When the pressure across the valve reverses and blood begins to flow in the reverse direction, the three leaflets engage each other in a coaptive region, occluding the valve body annulus and preventing the flow of blood through the valve in the reverse direction. The valve leaflets may be made from tissue, such as specially treated porcine or bovine pericardial tissue, or from man-made materials such as polyurethane, silicone rubber or other biocompatible polymer.

One of the issues considered in the design of heart valves incorporating flexible leaflets is the durability of the leaflets. When the valve is in a "closed" position (i.e., when it is closed and may be under a reverse pressure load) the leaflets experience stress. In addition, the valve commissure, which is the region where the leaflets contact the attachment curve and an adjacent leaflet, also experience high mechanical stress. The commissure is also the location of physical characteristics, called "stress risers," which increase the amount of stress on the leaflet near the commissure. For example, an edge of a tissue leaflet that has been cut by a knife blade often adjoins or is near the commissure. The trauma of being cut by a blade creates stress risers along the cut edge. Further, the commissure is an area where the flexible leaflet is coupled to the less flexible valve body, which create stress risers. Finally, the commissure has small radius corners that create stress risers.

Prior heart valve designs have incorporated flexible stents into the valve body to reduce the mechanical stress at the commissure. Another prior art approach to reducing mechanical stress is to incorporate non-isotropic materials, such as fabric, into the leaflets.

BRIEF SUMMARY OF THE INVENTION

The present invention is directed to a prosthetic heart valve with flexible leaflets. The leaflets have an analytic shape in a selected position which can be represented generally by analytic geometry. An analytic shape may include a portion of a cylindrical surface, of an ellipsoid, of a paraboloid, or of another shape that can be defined mathematically. The leaflets are coupled to a valve body at an attachment curve. The attachment curve is configured to distribute the stress experienced by the leaflet along the attachment curve when the leaflet is in a selected position. An annular valve body has a non-circular inner wall at least at the attachment curve, the shape of the inner wall being defined by the attachment curve. The invention increases the durability of a leaflet coupled to a valve body by moving the leaflet's point of maximum loaded stress along the attachment curve away from the location of stress risers.

The valve may further comprise a leaflet coupled to the leaflet support; the shape of the leaflet support being configured to locate a point of maximum stress on the leaflet away from a location of stress risers on the leaflet.

The invention may have a valve comprising a valve body and a first leaflet coupled to the valve body along an attachment curve. The attachment curve is configured to locate a point of maximum loaded stress on the first leaflet away from a location of stress risers on the first leaflet. The invention may also comprise a second leaflet and a commissure between the first leaflet and the second leaflet wherein the location of stress risers is the commissure.

The invention may also comprise a valve having a valve body and a leaflet coupled to the valve body along an attachment curve. The leaflet may comprise a surface and a free edge, the free edge comprising a center point. A region of maximum loaded stress may comprise a range of points along the attachment curve that are substantially an equal distance, measured along the surface of the leaflet, from the center point of the leaflet's free edge. The region of maximum loaded stress may be closer, measured along the surface of the leaflet, than any point along the attachment curve that is not among the points in the region of maximum loaded stress.

In general, in another aspect, the invention features a method of making a valve. An analytic shape for one or more flexible leaflets in a selected position is selected. An attachment curve for a leaflet is selected. Because the leaflet has an analytic shape, mathematical modeling (i.e., finite element analysis) may be used to predict stress at the attachment curve. The shape of the attachment curve is revised until predicted stress falls within acceptable design limits. A valve body is formed having a longitudinal axis in a direction of blood flow. An inner wall of the valve body is shaped to conform to the attachment curve. The leaflet is coupled to the valve body at the attachment curve.

In another aspect, the invention features a method of making a valve comprising selecting a leaflet having an analytic shape in a selected position. An attachment curve is selected. The attachment curve has a first end and a second end. The shortest distance along a surface of the leaflet from a center of a free edge of the leaflet to a point of maximum stress along the attachment curve is less than the distance along the surface of the leaflet from the center of the free edge of the leaflet to the first end of the attachment curve. A valve body is formed. The valve body has an inner wall conforming to the attachment curve and coupling the leaflet to the valve body along the attachment curve.

The invention may feature a valve comprising a valve body and a leaflet coupled to the valve body along an attachment curve. The attachment curve comprises a first end and a second end. The leaflet is movable between an open position and a closed position. The leaflet has a point of maximum displacement between the open and closed positions. The shortest distance along the surface of the leaflet from the point of maximum displacement to a point of maximum stress along the attachment curve is less than the distance along the surface of the leaflet from the point of maximum displacement to an end of the attachment curve. The point of maximum displacement may be a center of a free edge of the leaflet.

These and other features and advantages of the invention will be apparent from the following description and accompanying drawings.

DETAILED DESCRIPTION OF THE INVENTION

Figure 1:
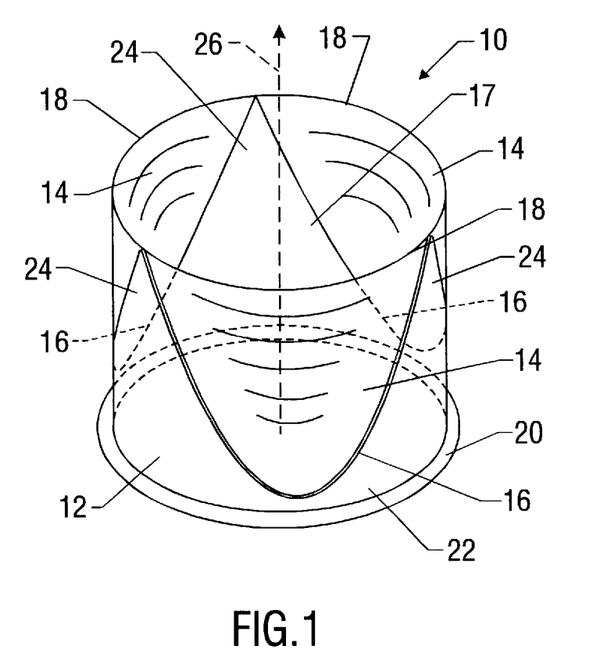
FIG. 1 is a perspective view of a tri-leaflet valve in the open position.

A tri-leaflet heart valve prosthesis 10 comprises an annular valve body 12 and three flexible leaflets 14 made of a biocompatible polymer such as silicone or polyurethane, as shown in FIG. 1, or of tissue. It is important that the leaflet material have an analytic shape in a selected position, as explained hereafter. The selected position is preferably a "no-load" position such that the leaflet is not distorted by pressures on the leaflet. The selected position of the leaflet may be closed, partially closed, or open with respect to the valve body. The selected position may be selected for ease of manufacturing. An analytic shape is a shape which can be represented generally by analytic geometry. An analytic shape may include a portion of a cylindrical surface, of an ellipsoid, of a paraboloid, or of another shape that can be defined mathematically. Typical production methods for polymer structures, such as molding or die casting, can produce leaflets having analytic shapes in a selected position. For polymer cardiac heart valves, the annular valve body and leaflets are typically molded as a single piece. Tissue, such as porcine or bovine pericardium, can also be formed into leaflets having an analytic shape in a selected position, if the tissue is fixed or cured on a mandrel or other structure imparting a shape to the leaflet. Gluteraldehyde may be used to fix the tissue, although other methods known in the art may also be used. The resulting leaflets will have a shape in a selected position which can be defined as a regular, axially symmetrical shape over at least a greater part of the leaflet. Such shapes include portions of cylinders, ellipsoids, paraboloids, or other shapes that can be similarly mathematically defined. Each leaflet is coupled to the valve body along an attachment curve 16. An inner wall 17 of the valve body conforms to the attachment curve adjacent the attachment curve. In the heart valve prosthesis of the invention, the inner wall 17, seen in top plan view, will be non-cylindrical at least in part, as explained in connection with FIG. 7, below.

Each leaflet has a free edge 18 that is not coupled to the valve body. A sewing ring 20 is coupled to the base of the valve body 12 and provides a place for sutures to be applied when the valve is implanted. The valve body comprises an annular base 22 and a leaflet support, comprising shaped posts 24, that supports the leaflets 14.

Figure 2:
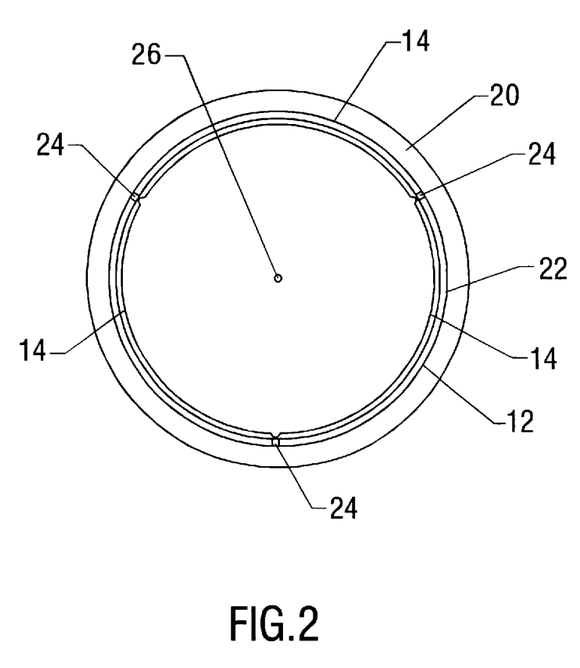
FIG. 2 is a plan view of the valve of FIG. 1.

When the pressure across the valve reverses and the blood begins to flow in the forward direction, i.e. in the direction of the arrow shown in FIG. 1, the pressure of the blood flow causes the leaflets 14 to deflect away from a central longitudinal axis 26 of the valve body that is generally parallel to the three posts 24. In this "open" position, the leaflets 14 define a large flow orifice, as shown in FIG. 2. With the leaflets in the open position shown in FIGS. 1 and 2, the valve presents little resistance to fluid flow.

Figure 3:
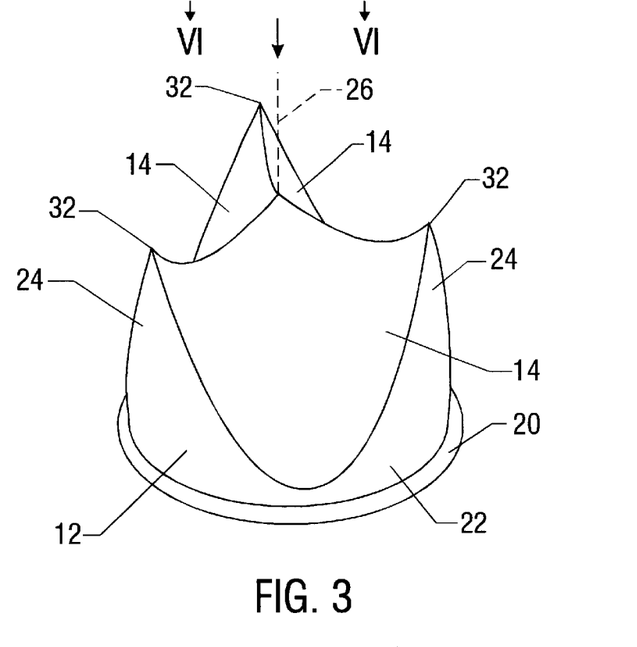
FIG. 3 is a perspective view of a tri-leaflet valve in the closed position.
Figure 4:
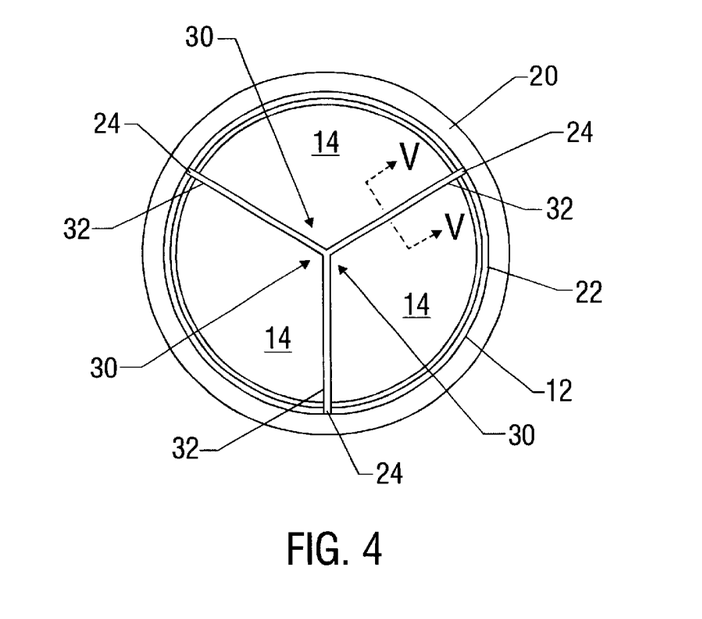
FIG. 4 is a plan view of the valve of FIG. 3.
Figure 5:
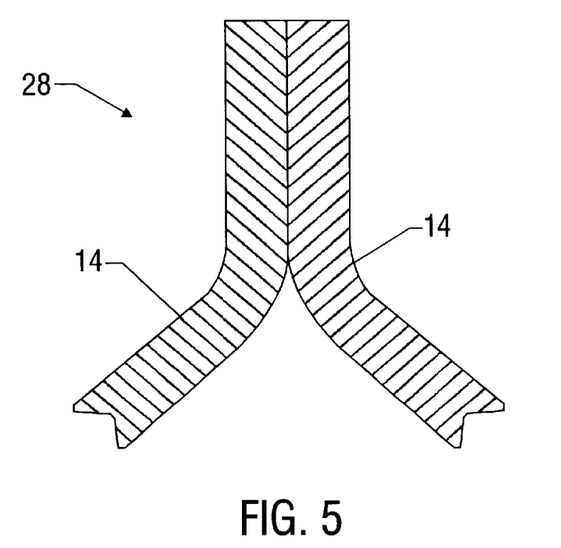
FIG. 5 is a cross-sectional view along lines V on FIG. 4.
Figure 6:
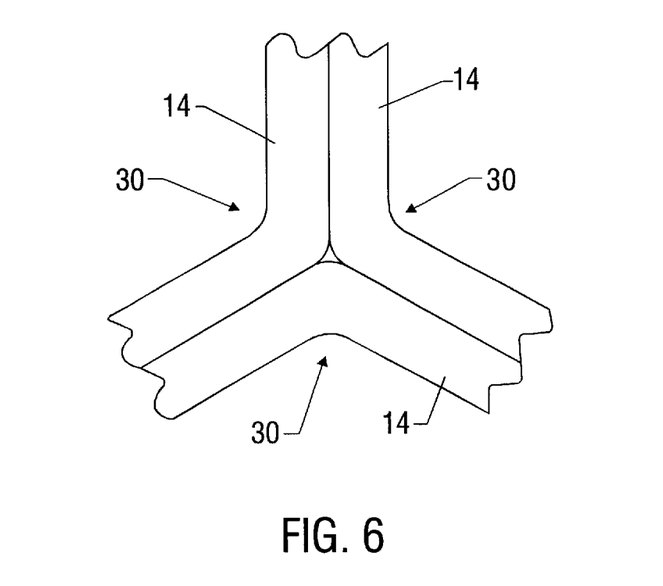
FIG. 6 is a view along lines VI on FIG. 3.

When fluid flow is in the reverse direction, i.e. in the direction of the arrow shown in FIG. 3, the pressure of the blood flow causes the leaflets to deflect toward axis 26, as shown in FIGS. 3 and 4. In this "closed" position, where the three leaflets are closed and are subject to a load in the reverse direction, each of the leaflets would occlude more than one-third of the valve body's orifice were it not for the presence of the other leaflets. Consequently, when the three leaflets deflect toward axis 26, they engage each other and form coaptive areas 28, as shown in FIG. 5, which help the valve seal against reverse flow. Further, when the leaflets press together, each leaflet forms a "triple point" 30 at the point where the three leaflets come together, as shown in FIG. 6.

The place where the leaflets 14 come together adjacent the posts 24 is called the "commissure" 32, as shown in FIG. 3. Each leaflet has a small bending radius in the vicinity of the commissure. For polymer valves, the flexible leaflets are generally manufactured by molding and cutting the leaflet along the free edge (including the commissure) to match design criteria. Both of these factors are stress risers, which makes the commissure 32 a location of high stress risers.

A point at or near a leaflet's triple point 30 experiences the maximum displacement of any point on the leaflet between the valve's open and closed position. If the leaflet is imagined as a collection of non-interconnecting spans connecting the triple point to the attachment curve, the triple-point end of each of those spans experiences the same displacement between the valve's open and closed positions. In the valve of the invention, the material properties of the leaflet should be chosen such that the leaflet can be reasonably modeled by an analytic shape, that is by a surface comprising a portion of a cylinder, an ellipsoid, a paraboloid, or other shape that can be similarly mathematically defined as a surface of rotation about an axis or as a surface symmetrical about a plane. If the selected position for the leaflets is the closed position, the small deflection of the leaflets resulting from the coaptive areas does not contribute significantly to the stress experienced by the leaflet. The maximum stress when the leaflet is in its selected position, or "maximum loaded stress", will occur along the span, measured along the surface of the leaflet, with the shortest original length.

In prior art prosthetic heart valves with flexible leaflets, the configuration of the attachment curve has not been selected with respect to an analytic shape of the leaflets. In general, the valve bodies have had a circular cross section, that is, a cylindrical inner wall. In some prior art designs, therefore, the span with the shortest original length connects the triple point 30 to the commissure 32, which means the point of maximum loaded stress will occur along this span. As discussed above, the commissure 32 is a location of high stress risers. The presence of both the point of maximum loaded stress and high stress risers at the commissure 32 increases the high likelihood that the leaflet will fail at the commissure 32.

Figure 13:
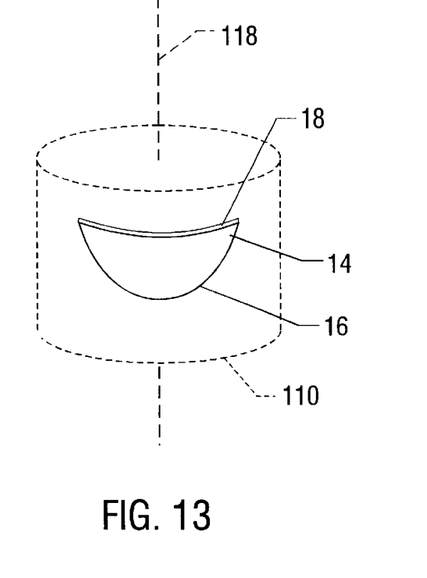
FIG. 13 and 14 are perspective views of valve leaflets illustrating a cylindrical analytical shape.
Figure 14:
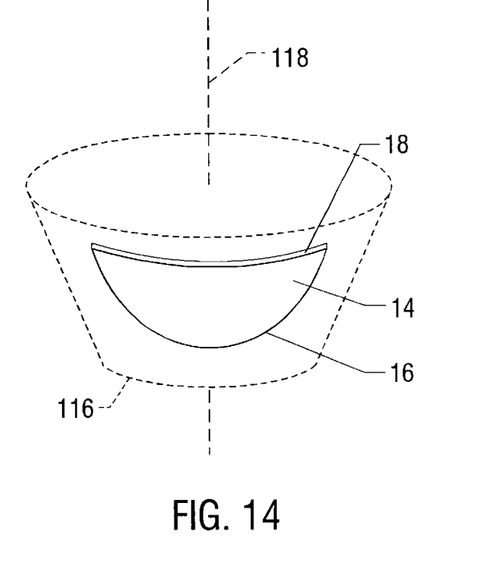
Figure 15:
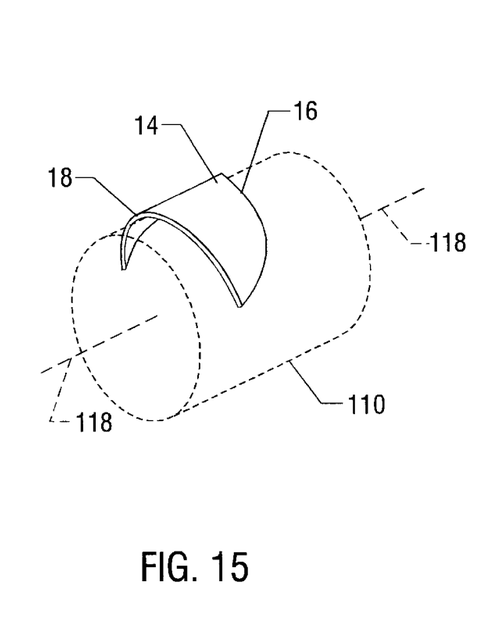
FIG. 15 is a perspective view of a valve leaflet illustrating a conical analytic shape.
Figure 16:
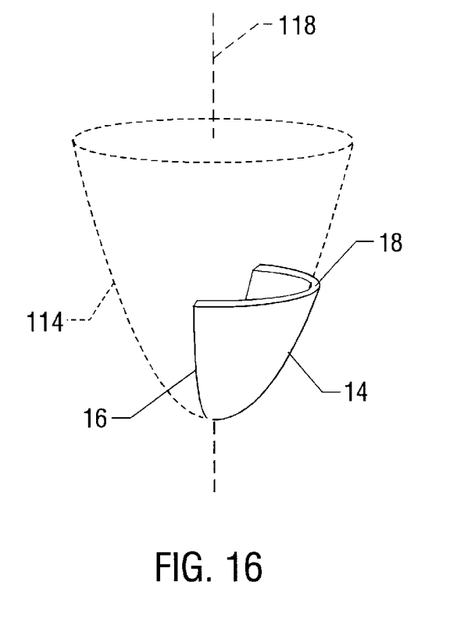
FIG. 16 is a perspective view of a valve leaflet illustrating a paraboloid analytic shape.
Figure 17:
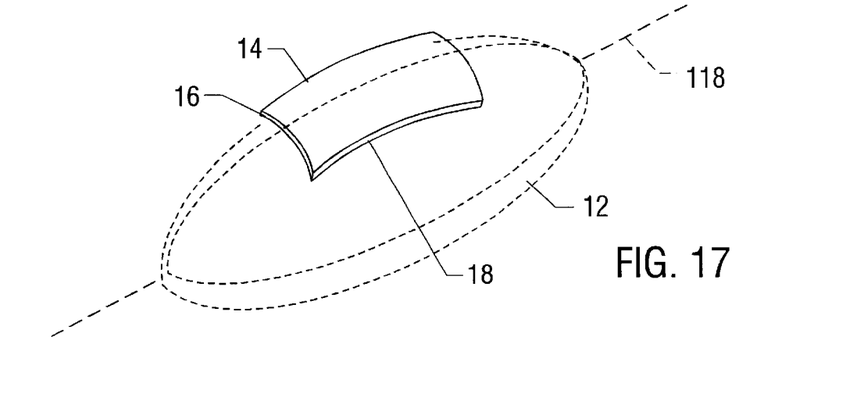
FIG. 17 is a perspective view of a valve leaflet illustrating an ellipsoid analytic shape.
Figures 18, 19:
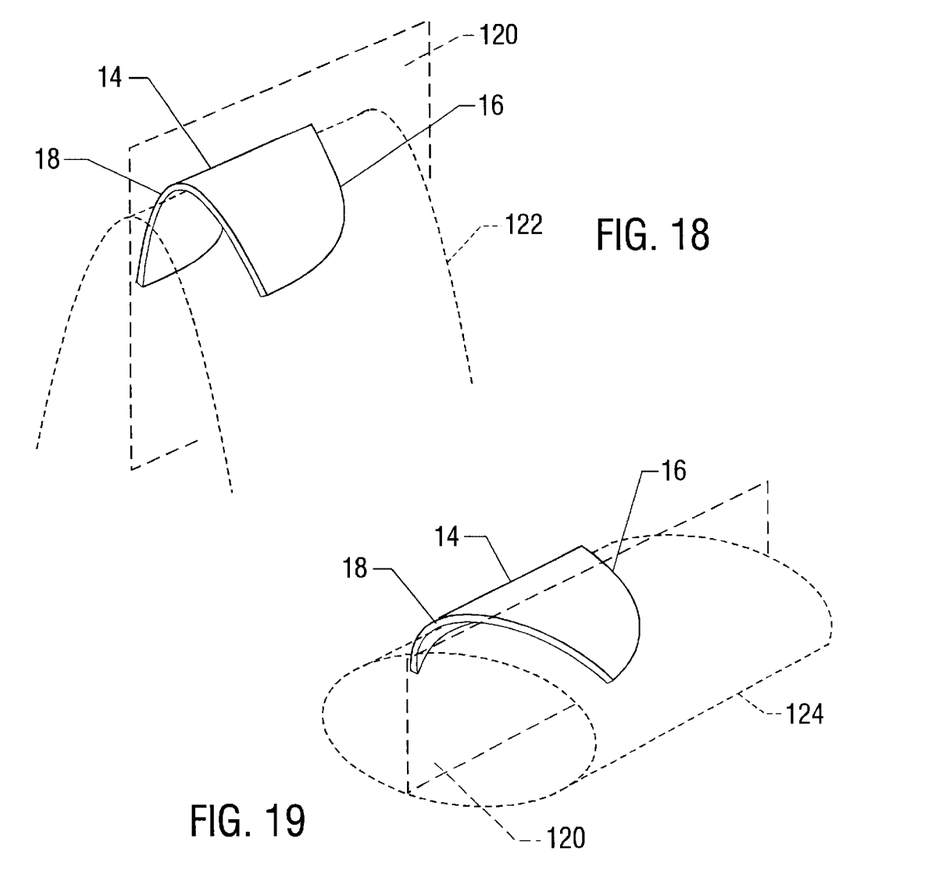
FIG. 18 is a perspective view of a valve leaflet illustrating a parabolic cylinder analytic shape.
FIG. 19 is a perspective view of a valve leaflet illustrating an elliptical cylinder.

In the prosthetic heart valves of the present invention, the valve leaflets 18 are given an analytic shape, such as a portion of a cylindrical surface 110 (FIG. 13 and FIG. 14), an ellipsoid 112 (FIG. 17), a paraboloid 114 (FIG. 16), or other shape that can be similarly mathematically defined. A portion of a conical surface 116 (FIG. 15) may also be used. The aforementioned shapes are generally symmetrical around an axis of symmetry 118. Shapes symmetrical about a plane of symmetry could also be used. Such shapes include parabolic cylinders 122 (i.e., a projection of a parabola out of an x-y plane along a z axis) or elliptical cylinders 124 (i.e., a projection of an ellipse out of an x-y plane along a z axis) or similar shapes. FIGS. 18 and 19 illustrate leaflets shapes on a parabolic cylinder and an elliptical cylinder respectively.

The material of the leaflets is selected such that the leaflets generally maintain this analytic shape in a selected position. Such material may be a polymer such as polyurethane or silicon rubber, or tissue such as porcine or bovine pericardium which has been cured in a particular shape, for example, on a mandrel. The shape of each leaflet is preferably a portion of a shape which would be symmetrical around an axis of symmetry 118 or a plane of symmetry 120 for that leaflet. In a tri-leaflet valve these axes or planes would usually be spaced at 120□ around an axis of flow through the triple point of the valve. An attachment curve for the leaflet is then selected. Because leaflets have an analytic shape, mathematical modeling can be used to predict the stress at the attachment curve.

The present invention reduces the likelihood of leaflet failure by moving the location of maximum loaded stress away from the location of stress risers, i.e. away from the commissures. In particular, the invention reduces the likelihood of leaflet failure by moving the location of maximum loaded stress away from the commissure 32. This is accomplished by changing the geometry of the attachment curve 16 so that the shortest distance along the surface of the leaflet from the triple point 30 to the attachment curve 16 is not along the leaflet's free edge 18. This moves the location of the point of maximum loaded stress away from the free edge 18 and away from the commissure 32. The configuration of the valve body, and in particular the shape of the inner wall 17 of the valve body adjacent the attachment curve, is selected to conform to the attachment curve. Sections of the valve body in planes perpendicular to the axis of flow and intersecting the attachment curve will usually disclose a non-circular shape for the inner wall of the valve body. A projection of the attachment curve onto a plane perpendicular to the axis of flow will also be non-circular. The inner wall 17 of the valve body may transition to circular or elliptical away from the attachment curve. In addition, an outer wall of the valve body may have a cylindrical, elliptical, or other configuration without affecting the attachment curve between a leaflet and the valve body.

Figure 7:
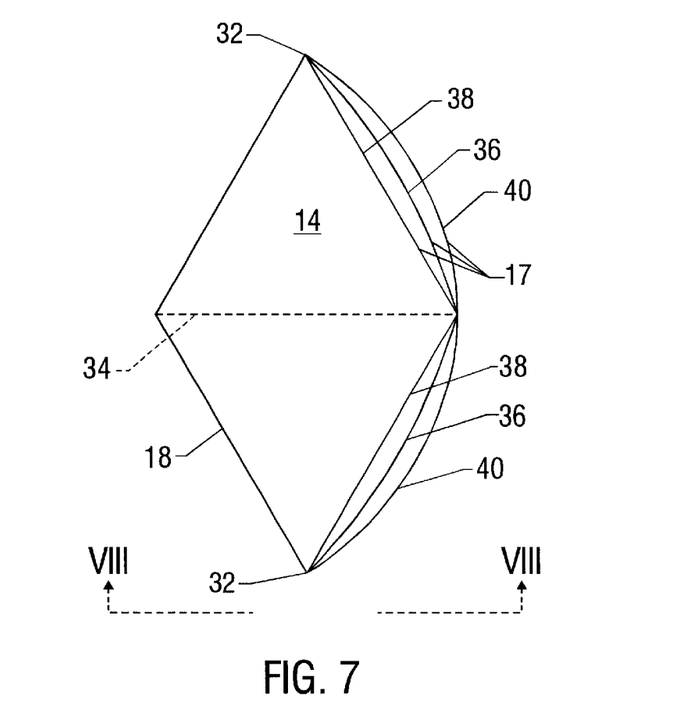
FIG. 7 is a plan view of a leaflet.
Figure 8:
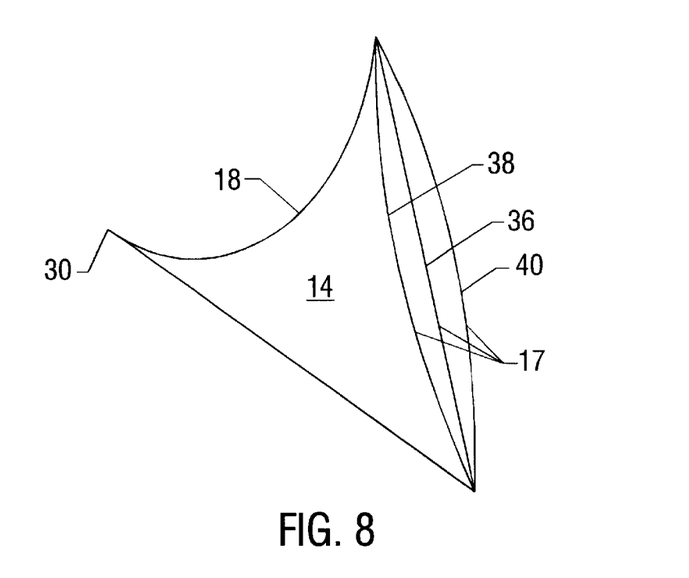
FIG. 8 is an elevation view of a leaflet, viewed along lines VIII on FIG. 7.
Figures 20, 21:
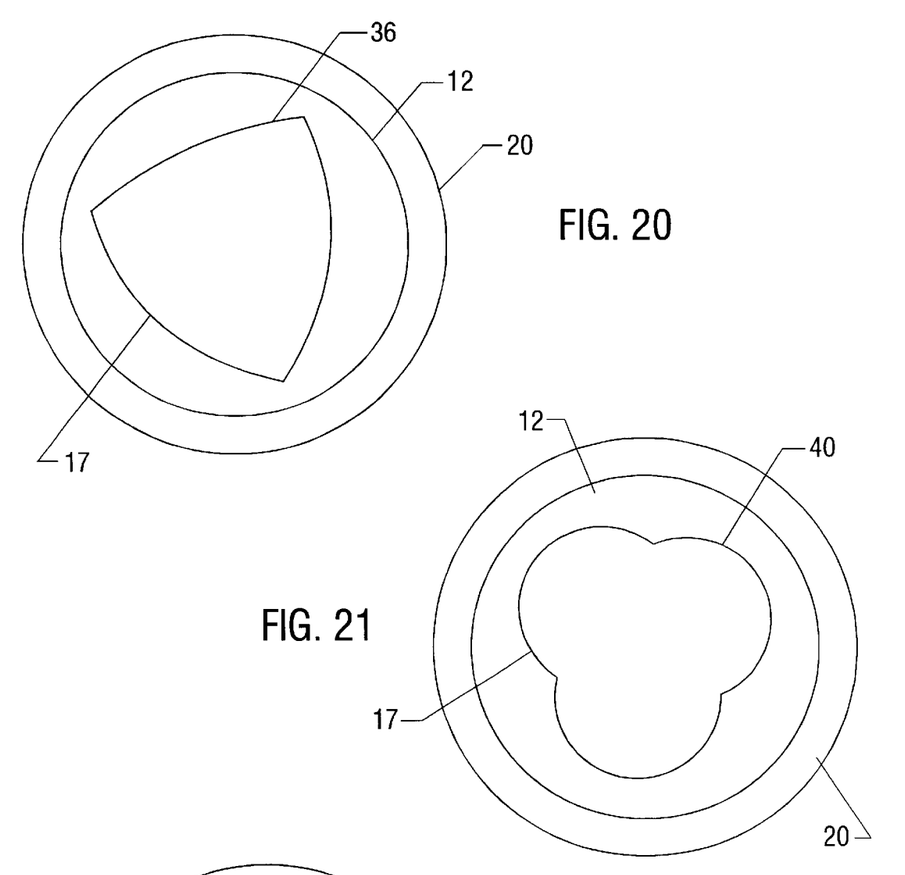
FIGS. 20, 21 and 22 are top plan views of a valve showing a feature of an inner wall, in highly exaggerated scale.

The location of the point of maximum loaded stress may be moved by changing the geometry of the attachment curve. The geometry of the attachment curve, where the geometry of the leaflet 14 is defined or pre-selected, determines the geometry of the inner wall of the valve body 12. If the leaflet shape is held constant, the attachment curve which produces a cylindrical inner wall 36 of a valve body is different than one which produces a non-cylindrical inner wall of a valve body. For example, an attachment curve may be selected that produces an inner wall of the valve body that is either convex 38 or concave 40 relative to cylindrical, as illustrated in FIGS. 7 and 8. Leaflet 14 is symmetrical around midline 34. A first attachment curve may produce a circular inner wall 36 of the valve body. A second attachment curve may produce an inner wall 38 of the valve body that is concave relative to a cylindrical shape. This may produce, for example, an inner wall 36 which may be represented by a polygon with curved faces, as shown in FIG. 20, in highly exaggerated scale. A third attachment curve may produce an inner wall 40 of the valve body which has a shape that is convex relative to a cylindrical shape, for example. This shape of the inner wall may also be characterized as a polygon, but with faces that bulge out beyond a radial distance containing the vertices of the polygon, as shown in FIG. 21, also in highly exaggerated scale.

In the past, heart valves with flexible leaflets have been designed by selecting a design for an attachment curve and then forming the attachment curve, often embodied in a stent, around the valve body, which was usually provided with a cylindrical inner wall, or other cylindrical structure for supporting the stent. The leaflets were then provided to occlude the orifice. The shape and dimensions of the leaflets were not the primary design parameters. In the present invention, an analytic shape of the leaflet is selected first. Then the dimensions of the leaflet are determined by selecting an attachment curve. Because the analytic shape of the leaflet has been pre-selected, the stresses along the attachment curve can be calculated and an attachment curve can be selected which distributes and reduces stresses. The selection of the analytic shape of the leaflet and the attachment curve determines the shape of the inner wall of the valve body, which is non-cylindrical in a preferred embodiment.

Figure 9:
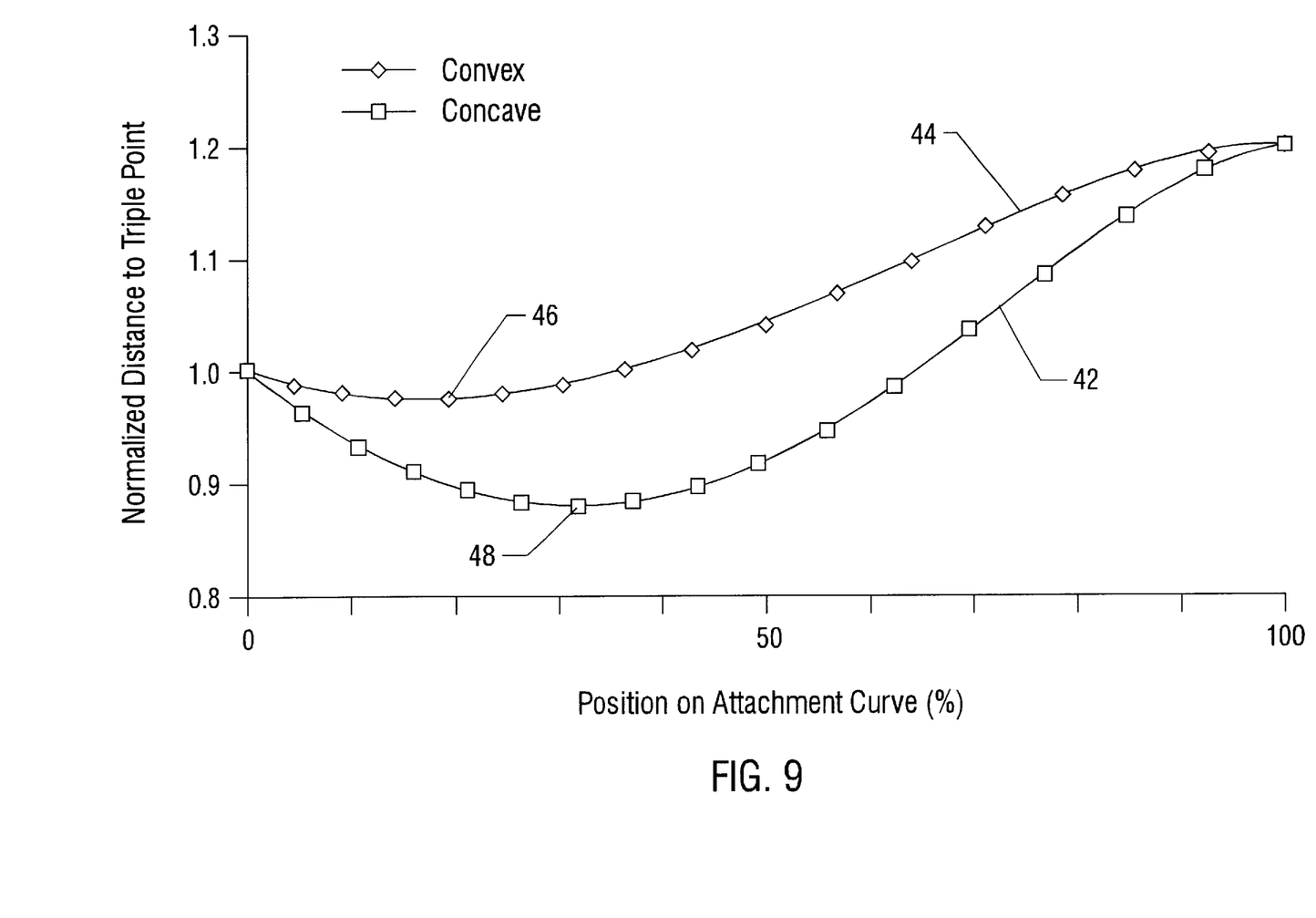
FIG. 9 is a graph of a normalized distance to the triple point vs. position on the attachment curve.

Because the analytic shape of the leaflet is selected first, distances from the triple point to the attachment curve along the surface of the leaflet can be calculated. The distance from the triple point to the attachment curve for inner wall 38 is different than the distance from the triple point to attachment curve for inner wall 40, as illustrated in FIG. 9, for a cylindrical analytic shape for the leaflet. In FIG. 9, the vertical axis is the normalized distance from the triple point to the attachment curve along a leaflet having a cylindrical analytical shape, with the normalization factor being the distance from the triple point to the commissure. The horizontal axis represents the edge position, measured as a percentage of the arc from the commissure to the intersection of the leaflet midline 34 with the attachment curve. Thus, for example, the commissure is at zero percent and the intersection of the midline 34 with the attachment curve is at one-hundred percent. Half way along the attachment curve between those two points is fifty percent.

Curve 42 illustrates the normalized distance along the surface of the leaflet between the triple point and each point on the concave attachment curve 38. Curve 44 illustrates the normalized distance along the surface of the leaflet between the triple point and each point on the convex attachment curve 40. A distance along the leaflet can be determined because the leaflets have an analytic shape. Since the distance along the leaflet from the triple point to a point on the attachment curve is inversely proportional to the stress at that point on the attachment curve, in the absence of stress risers a curve may be selected which distributes the stress away from stress risers, i.e., away from the commissures, and which smooths the stress distribution. On curve 44, the minimum distance point 46 occurs at approximately twenty percent and has a normalized value just less than 1.0. On curve 42, the minimum distance point 48 occurs at approximately thirty percent and has a normalized value of less than 0.9. Thus, the minimum distance along the surface of the leaflet from the triple point to the attachment curve is different for attachment curve 38 than it is for attachment curve 40 (FIG. 7). Further, the minimum distance point is in a different location along the attachment curve for attachment curve 38 than it is for attachment curve 40.

Figure 10:
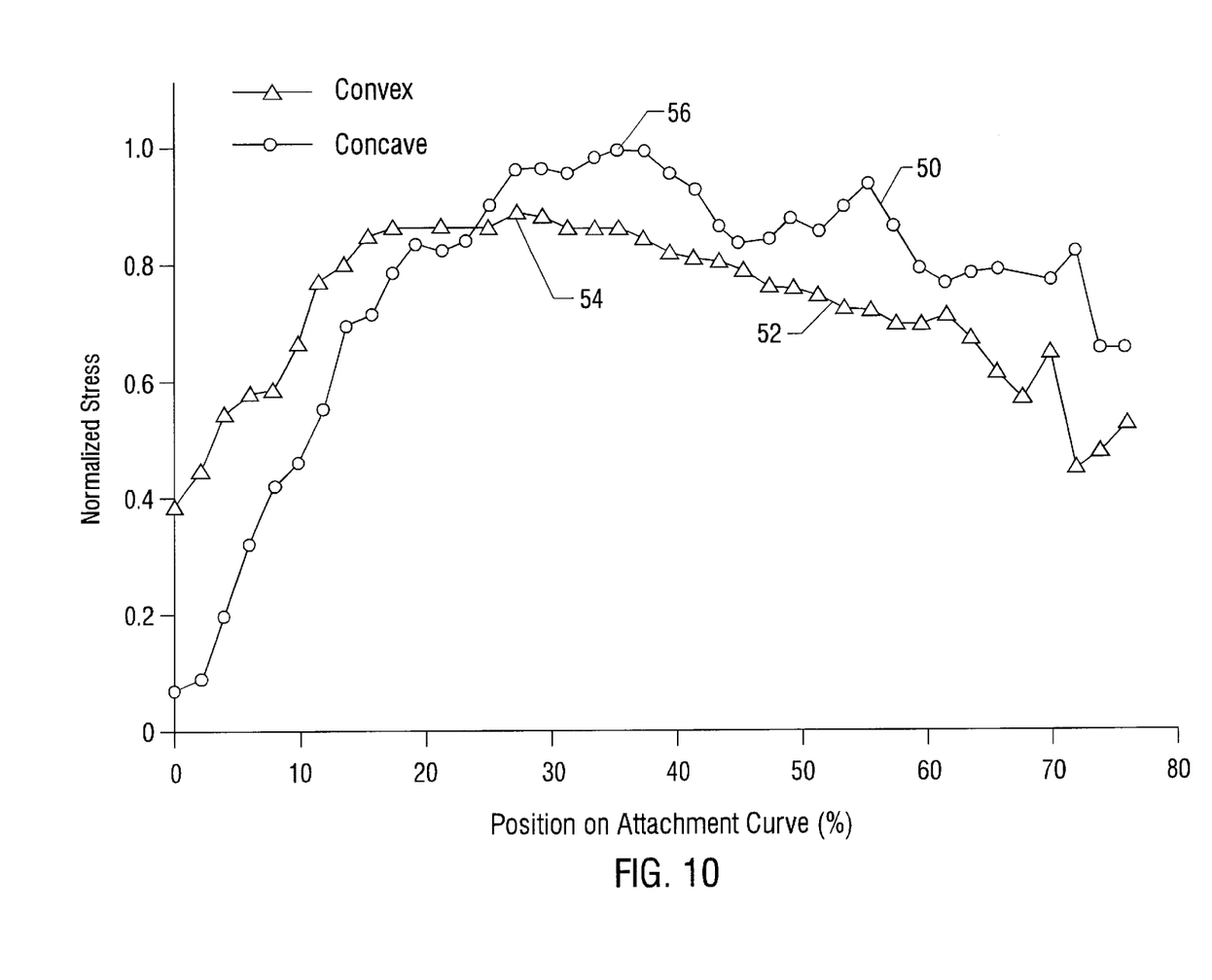
FIG. 10 is a graph of normalized stress vs. edge position.

Because of these differences in the minimum distance and the position of the minimum distance point, the point of maximum loaded stress along the attachment curve is different for attachment curves 38 and 40, as illustrated in FIG. 10. The chart in FIG. 10 has a vertical axis representing normalized stress with the normalization factor being the maximum stress shown on the Figure. The horizontal axis is the same as the horizontal axis in FIG. 9.

Curve 50 illustrates the loaded stress along convex attachment curve 40. Curves 50 and 52 were produced by performing a finite element analysis of the respective geometries of the convex and concave leaflet designs.

As can be seen from FIG. 10, the point of maximum loaded stress 54 on convex attachment curve 52 occurs between the twenty- and thirty-degree points and experiences a normalized stress of approximately 0.90. The point of maximum loaded stress 56 on concave attachment curve 50 occurs between the thirty- and forty-degree points and experiences a normalized stress of 1.0. This demonstrates that the point of maximum loaded stress can be moved and the amount of stress that point experiences can be changed by changing the geometry of the attachment curve which results in modification of the valve body geometry, specifically through modification of the inner wall of the valve body.

Figure 11:
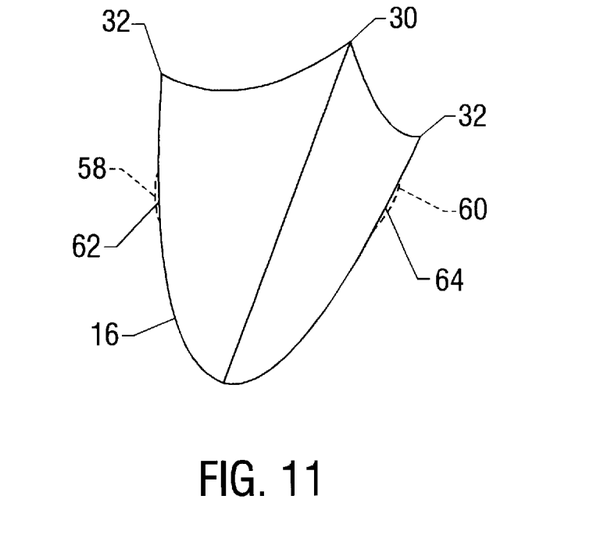
FIG. 11 is a perspective view of a leaflet having regions of maximum loaded stress.
Figure 22:
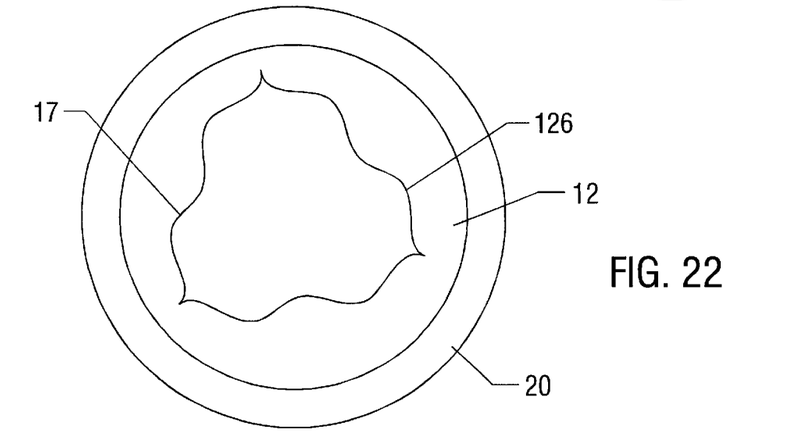

The magnitude of the maximum loaded stress can be further modified by changing the attachment curve to increase the distance from the leaflet's point of maximum displacement (or triple point) to "regions" 58, 60 in the vicinity of points of maximum loaded stress 62, 64 on the leaflet's attachment curve, as shown in FIG. 11. This means that the inner wall of the valve body would have a complex shape, determined by the distances along the leaflet from the triple point. Such a shape 126 is illustrated in FIG. 22, in highly exaggerated scale. This change in shape may cause the point of maximum loaded stress to change location, which may make it necessary to change the geometry of the attachment curve to reposition the point of maximum loaded stress once again. If necessary, the design of the attachment curve and the distance from the point of maximum displacement of the triple point can be iteratively revised until design criteria are met. Once the shape of the attachment curve has been determined, the adjacent inner wall of the valve body is configured to intersect the attachment curve.

Further, the maximum loaded stress can be spread over the regions 58 and 60 of the leaflet by designing the attachment curve so that the regions 58 and 60 are equally distant from the point of maximum displacement of the triple point. The result would be a region of points experiencing maximum loaded stress rather than a single point, further reducing the likelihood of leaflet failure at the single point.

In the preferred embodiment, the leaflet geometry is circularly cylindrical and the attachment curve produces a valve body geometry which is convex of cylindrical such as curve 40 illustrated in FIGS. 7 and 8.

Figure 12:
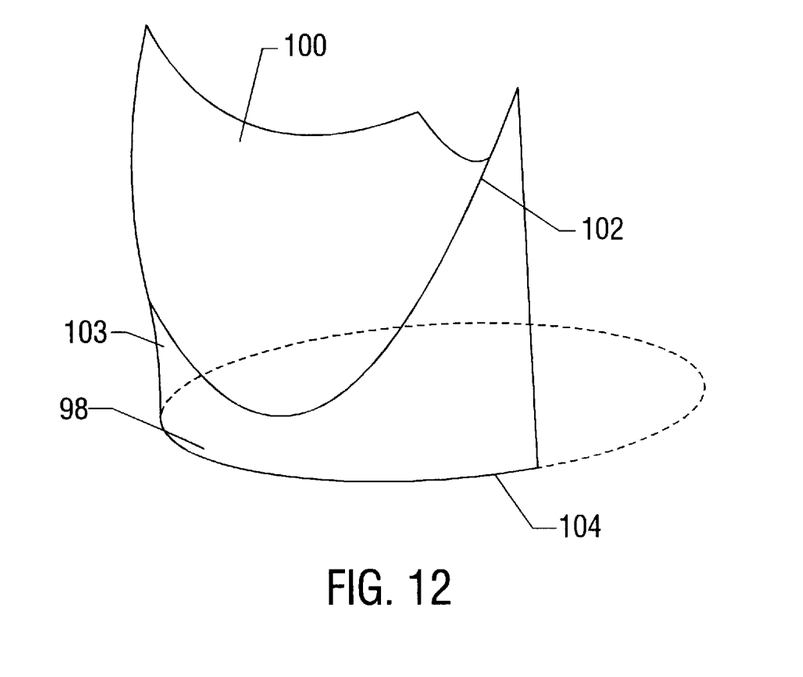
FIG. 12 is a perspective view of a portion of a valve.

In an alternative embodiment, an example of which is illustrated in FIG. 12, the valve body 98 has a different shape at the elevation of the attachment curve than its shape at its base. In FIG. 12, leaflet 100 is coupled to valve body 98 along attachment curve 102. The inner wall 103 of the valve body is non-circular near the attachment curve. The inner wall at the base of the valve body 100 has a circular shape 104. The attachment curve 102 is shaped so that its projection onto the plane containing circle 104 is not a circle. Thus, the attachment curve 102 can be shaped to locate the point of maximum loaded stress to meet design requirements and the inner wall of the valve body can be shaped to intersect the selected attachment curve while not affecting other design parameters, such as the shape of the valve body 12 where the sewing ring is coupled to it.

The foregoing describes preferred embodiments of the invention and is given by way of example only. For example, the invention is not limited to heart valve technology but is equally applicable to any valve with flexible leaflet occulders. The invention is not limited to any of the specific features described herein, but includes all variations thereof within the scope of the appended claims.

What is claimed is:

1. A valve comprising:

a valve body having an inflow end, an outflow end, and an inner wall extending between the inflow end and the outflow end forming an orifice having a longitudinal dimension along an axis extending between the inflow end and the outflow end;

at least one flexible leaflet having an analytic shape in a selected position coupled to the inner wall along an attachment curve; and wherein a portion of the inner wall intersecting the attachment curve has a noncylindrical shape in a plane perpendicular to the longitudinal axis of the orifice.

2. A valve comprising a valve body having an inner wall defining an orifice;

at least one flexible leaflet having an analytic shape in a selected position wherein the leaflet has a surface and a free edge, with the free edge having a center point; and an attachment curve having a first end and a second end, the leaflet being coupled to the valve body along the attachment curve at the inner wall, the inner wall being non-cylindrical along said attachment curve and wherein the attachment curve is configured to have a shortest distance measured along the surface of the leaflet between the center point of the free edge and a point on the attachment curve, said point being removed from both the first end and the second end of the attachment curve, said shortest distance being smaller than both the distance measured along the surface of the leaflet between the center point of the free edge and the first end of the attachment curve and the distance measured along the surface of the leaflet between the center point of the free edge and the second end of the attachment curve.

3. The valve of claim 2 wherein a region along said attachment curve shares said shortest distance.

4. The valve of claim 2 wherein said analytic shape comprises a portion of a cylindrical surface.

5. The valve of claim 2 wherein said analytic shape comprises a portion of an ellipsoid.

6. The valve of claim 2 wherein said analytic shape comprises a portion of a paraboloid.

7. The valve of claim 2 comprising three leaflets, each leaflet having an analytic shape in a selected position.

8. The valve of claim 2 wherein the inner wall is concave along the attachment curve.

9. The valve of claim 2 wherein the inner wall is convex along the attachment curve.

10. A method for making a valve comprising:

selecting at least one flexible leaflet having an analytic shape in a selected position;

forming a valve body having an inflow end, an outflow end, and an inner wall extending between the inflow end and the outflow end which forms an orifice having a longitudinal dimension along an axis extending between the inflow end and the outflow end; and coupling said leaflet to said inner wall along an attachment curve wherein a portion of the inner wall intersecting the attachment curve has a non-cylindrical shape in a plane perpendicular to the longitudinal axis of the orifice.

11. A method of making a valve comprising:

selecting a leaflet having an analytic shape in a selected position wherein said leaflet has a surface and a free edge, with the free edge having a center point;

connecting said leaflet to a valve body along an attachment curve having a first end and a second end;

configuring the valve body with an inner wall, said inner wall having a non-cylindrical surface defined by said attachment curve; and configuring the attachment curve to have a shortest distance measured along the surface of the leaflet between the center point of the free edge and a point on the attachment curve, said point being removed from both the first end and the second end of the attachment curve, said shortest distance being smaller than both the distance measured along the surface of the leaflet between the center point of the free edge and the first end of the attachment curve and the distance measured along the surface of the leaflet between the center point of the free edge and the second end of the attachment curve.

12. The method of claim 11 wherein a region of said attachment curve shares said shortest distance.

13. The method of claim 11 wherein said analytic shape comprises a portion of a cylindrical surface.

14. The method of claim 11 wherein said analytic shape comprises an ellipsoid.

15. The method of claim 11 wherein said analytic shape comprises a paraboloid.

16. The method of claim 11 wherein configuring said attachment curve includes locating a point of maximum stress on the leaflet away from commissures.

17. The method of claim 11 further comprising selecting three leaflets, each leaflet having an analytic shape in selected position.

18. The method of claim 11 wherein said leaflet has a surface and a free edge, the free edge having a center point; and said attachment curve has a first end, a second end and a point of maximum stress between said first and second ends, said method further comprising:

calculating a calculated point on a calculated attachment curve defined by the intersection of the leaflet and a hypothetical circular inner wall, which calculated point is calculated to experience maximum stress under load; and configuring the attachment curve so that a linear distance between said center point and said point of maximum stress is greater than a linear distance between said center point and said calculated point, said point of maximum stress being co-linear with said center point and said calculated point.

19. The method of claim 18 increasing a linear distance between said center point and said attachment curve beyond said calculated attachment curve for a region around said point of maximum stress.

* * * * *

UNITED STATES PATENT AND TRADEMARK OFFICE
CERTIFICATE OF CORRECTION

PATENT NO.    : 6,613,086 B1                                       Page 1 of 1
DATED         : September 2, 2003
INVENTOR(S)   : Riyad E. Moe and John Kenneth Ryder It is certified that error appears in the above-identified patent and that said Letters Patent is hereby corrected as shown below:

Column 9,
Lines 4, 12 and 48, delete "flexible" and insert -- made of flexible material -- after "leaflet".

Column 10,
Line 2, insert -- made of flexible material -- after "leaflet".
Line 54, insert -- including -- before "increasing".

Signed and Sealed this

Twenty-eighth Day of October, 2003

JAMES E. ROGAN
*Director of the United States Patent and Trademark Office*